(12) United States Patent
Rickert et al.

(10) Patent No.: US 8,361,017 B2
(45) Date of Patent: Jan. 29, 2013

(54) BALLOON CATHETER

(75) Inventors: Martin Rickert, Rottweil (DE); Boris Warnack, Mountain View, CA (US)

(73) Assignee: Abbott Laboratories Vascular Enterprises Limited, Dublin (IE)

( * ) Notice: Subject to any disclaimer, the term of this patent is extended or adjusted under 35 U.S.C. 154(b) by 0 days.

(21) Appl. No.: 13/055,348

(22) PCT Filed: May 18, 2009

(86) PCT No.: PCT/EP2009/003527
§ 371 (c)(1),
(2), (4) Date: Apr. 25, 2011

(87) PCT Pub. No.: WO2010/009784
PCT Pub. Date: Jan. 28, 2010

(65) Prior Publication Data
US 2011/0196296 A1 Aug. 11, 2011

(30) Foreign Application Priority Data
Jul. 23, 2008 (EP) .................................... 08013293

(51) Int. Cl.
*A61M 25/10* (2006.01)
(52) U.S. Cl. ................................................. 604/103.14
(58) Field of Classification Search ............... 604/96.01, 604/103.06, 103.1, 103.14; 606/159, 172, 606/174; 623/1.11
See application file for complete search history.

(56) References Cited

U.S. PATENT DOCUMENTS

| | | | |
|---|---|---|---|
| 5,458,572 A | 10/1995 | Campbell et al. | |
| 5,512,051 A * | 4/1996 | Wang et al. | 604/103.14 |
| 5,964,778 A * | 10/1999 | Fugoso et al. | 606/194 |
| 6,071,285 A * | 6/2000 | Lashinski et al. | 623/1.11 |
| 6,126,652 A * | 10/2000 | McLeod et al. | 606/1 |
| 6,425,882 B1 | 7/2002 | Vigil | |
| 6,623,451 B2 * | 9/2003 | Vigil | 604/99.01 |
| 7,491,188 B2 * | 2/2009 | Holman et al. | 604/103.01 |
| 7,896,840 B2 * | 3/2011 | Spencer et al. | 604/130 |
| 7,976,496 B2 * | 7/2011 | Kennedy et al. | 604/99.01 |
| 2006/0079836 A1 | 4/2006 | Holman et al. | |
| 2006/0129045 A1 * | 6/2006 | Warnack et al. | 600/435 |
| 2007/0156166 A1 | 7/2007 | Wu et al. | |
| 2007/0244501 A1 | 10/2007 | Horn et al. | |
| 2008/0249464 A1 * | 10/2008 | Spencer et al. | 604/103 |

FOREIGN PATENT DOCUMENTS
WO    WO 2010/009784    1/2010

* cited by examiner

*Primary Examiner* — Nicholas Lucchesi
*Assistant Examiner* — Aarti B Berdichevsky
(74) *Attorney, Agent, or Firm* — Workman Nydegger; Jonathan Feuchtwang

(57) ABSTRACT

A balloon catheter comprising a catheter tube, an inflatable and deflatable balloon fixed to the catheter tube and a refolding device for folding the balloon onto the catheter tube during balloon deflation, wherein the refolding device includes at least one flap arrangement being fixed on the catheter tube and being disposed within the balloon.

22 Claims, 4 Drawing Sheets

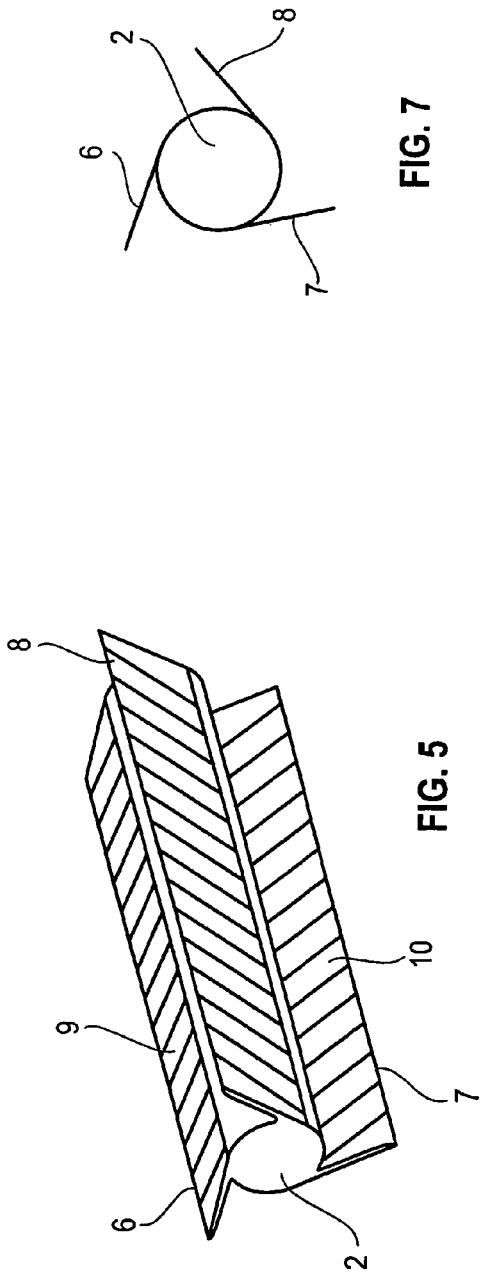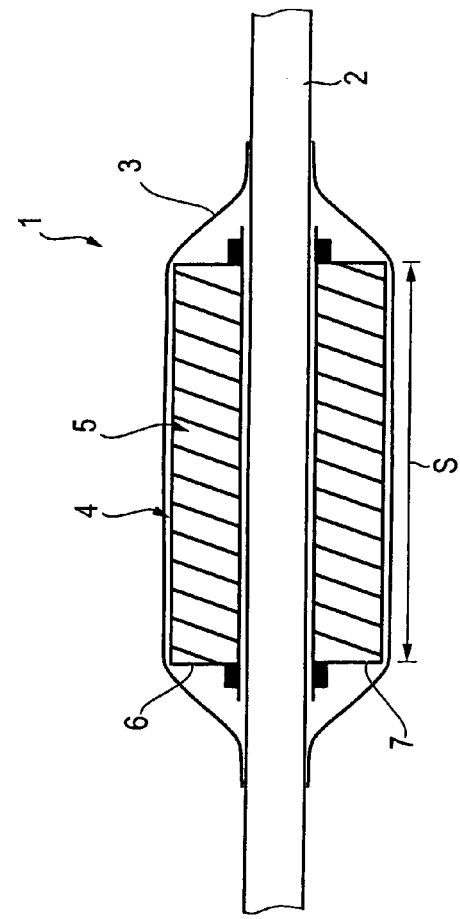

BALLOON CATHETER

CROSS-REFERENCE TO RELATED APPLICATIONS

This application is a U.S. Nationalization of PCT Application Number PCT/EP2009/003527 filed May 18, 2009 which claims the benefit of European Patent Application No. 08013293.9 filed Jul. 23, 2008, the entireties of which are incorporated herein by reference.

BACKGROUND

1. Field of the Invention

The present invention relates to a balloon catheter and particularly to a balloon catheter including a refolding device for folding the balloon onto the catheter tube during balloon deflation.

2. Relevant Technology

Various techniques and balloon structures have been developed for a defined or predictable folding during balloon deflation. For example U.S. Pat. No. 6,623,451 B2 describes a balloon catheter with a device including a band and a plurality of elongated fingers attached to the band to fold the balloon in a uniform and predictable manner during balloon deflation. However, the disclosed device is adapted neither to expand the balloon equally or symmetrically along the entire internal length of the balloon nor to assure a defined and equal refolding in all spatial directions without causing a so called "pancake-folding" or other folding failure.

BRIEF SUMMARY

It is, therefore, an object underlying the present invention to provide a balloon catheter including a refolding device that is able to solve the above mentioned problem and secures a defined and guided refolding of the balloon during balloon deflation.

The solution of this object is achieved by at least one embodiment of the present invention. The balloon catheter according to an embodiment of the present invention includes a catheter tube, an inflatable and deflatable balloon fixed to the catheter tube and a refolding device for folding the balloon onto the catheter tube during balloon deflation. The refolding device includes at least one flap arrangement being fixed on the catheter tube and being disposed within the balloon.

According to one embodiment of the present invention, the flap arrangement extends between Ro-markers disposed on the catheter tube and the flap arrangement includes at least three flexible flaps. These flaps are fixed and equally spaced from each other on the catheter tube and extend along a region of the catheter tube disposed in the balloon. The flaps are formed with predetermined lengths and formed in a bent or angled shape having decreasing cross sections along projecting lengths thereof.

According to a second embodiment of the present invention, the flap arrangement takes a linear symmetrical wave form with longitudinally increasing/decreasing lengths of flaps.

According to a further embodiment of the present invention, the flap arrangement takes a linearly offset wave form with longitudinally increasing/decreasing lengths of flaps.

Moreover, the flap arrangement can be fixed on a flap tube fixed on the catheter tube of the balloon catheter according to one embodiment of the present invention.

BRIEF DESCRIPTION OF THE DRAWINGS

Further features and advantages of the present invention will become apparent from the following description of preferred embodiments with reference to the appended drawings, wherein

FIG. 5 illustrates an isometric view of the balloon catheter with balloon folding mechanism.

FIG. 6 illustrates an enlarged cross sectional view of the balloon catheter in an inflated state according to a further embodiment of the invention.

FIG. 7 shows a cross-sectional view of a further flap arrangement according to another embodiment of the present invention.

DETAILED DESCRIPTION

Figure 1:
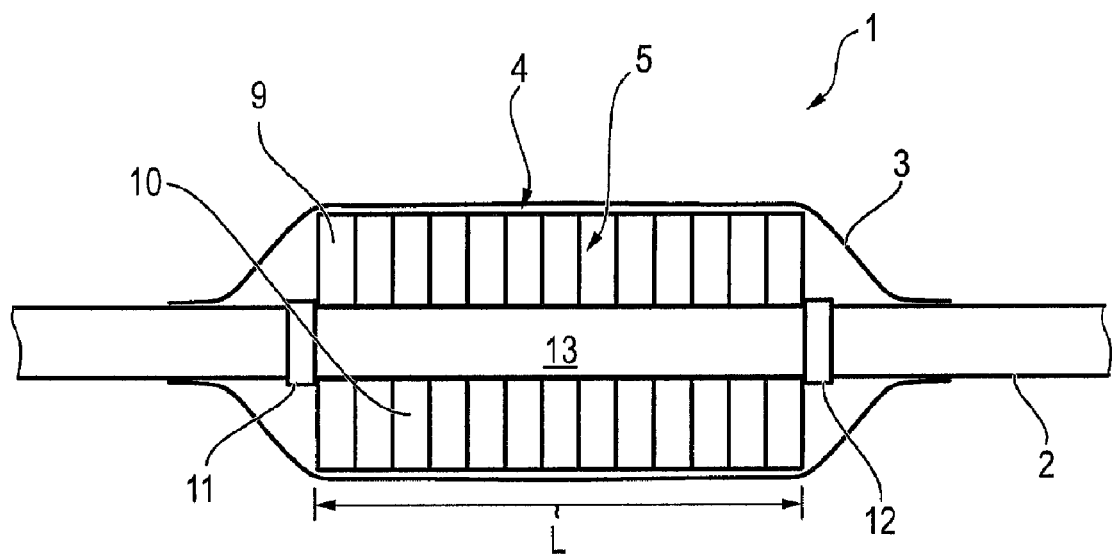
FIG. 1 shows an enlarged simplified cross sectional view of the balloon catheter 1 in an inflated state according to a first embodiment of the present invention.

In FIG. 1, an enlarged cross sectional view of the balloon catheter 1 according to a first embodiment of the present invention is depicted in an inflated state. The balloon catheter 1 includes a catheter tube 2, (which may include an inflation lumen and a guide wire lumen (either juxtaposed or in a concentric arrangement)) an inflatable and deflatable balloon 3 fixed on the catheter tube 2 and a refolding device 4 for folding the balloon 3 onto the catheter tube 1. The refolding device 4 disposed within the balloon 3 includes at least one flap arrangement 5 fixed on the catheter tube 2 having a plurality of flaps and in this case includes three flaps being separated into thirteen flap-portions 9, 10. The flap arrangement 5 has a length L in accordance with the size of the balloon 3 and extends along a region 13 of the catheter tube 2 between two Ro-markers 11, 12 disposed on the catheter tube 2.

Figure 2:
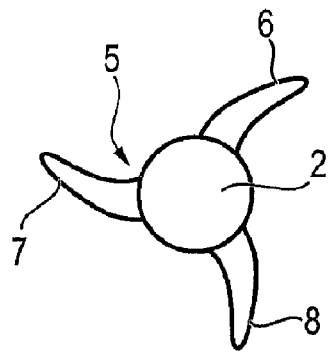
FIG. 2 shows an enlarged cross sectional view of the flap arrangement within the balloon catheter.

FIG. 2 shows an enlarged cross sectional view of the flap arrangement 5 according to an embodiment of the present invention. As shown in FIG. 2, three radially extending flexible flaps 6, 7, 8 are circumferentially fixed and equally spaced from each other on the catheter tube 2. However, the present invention is not limited to the number of flaps depicted herein and also an increased number of flaps can be provided without deviating from the scope of the invention. The flaps 6, 7, 8 comprise a predetermined length adapted to the respective dimension of the balloon 3 and are formed in a bent or angled shape. Moreover, the flaps are provided with decreasing cross sections along their projecting lengths to further increase their flexibility and to improve and assist a supported and guided refolding in all directions during deflation of the balloon 3.

Figure 3:
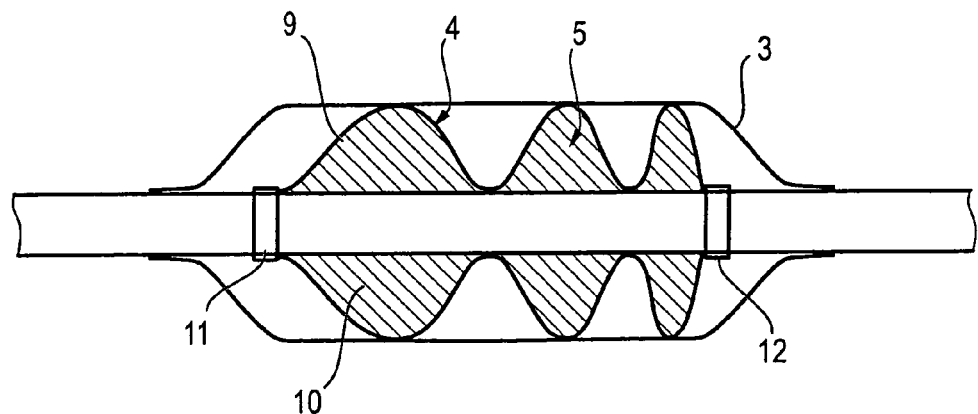
FIG. 3 shows an enlarged cross sectional view of the balloon catheter 1 in an inflated state according to a further embodiment of the present invention.

FIG. 3 illustrates an enlarged cross sectional view of the balloon catheter 1 in an inflated state according to a further embodiment of the present invention. In this embodiment, the flap arrangement 5 of the refolding device 4 arranged between the Ro-markers 11, 12 takes a linear symmetrical wave form with longitudinally increasing/decreasing lengths of flaps 9, 10. Due to this design and profiling of the flap arrangement 5, using less material for the included flaps the profile of the balloon catheter 1 in its deflated state is reduced to further facilitate the deployment of the balloon catheter 1 into small body vessels.

Figure 4:
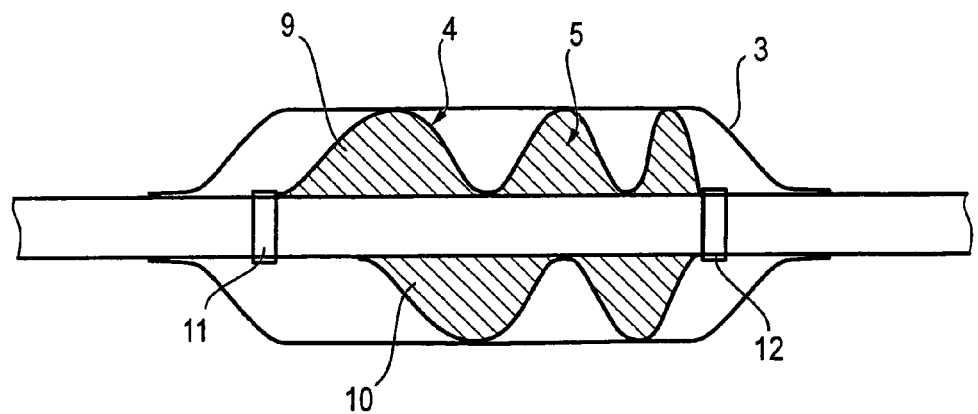
FIG. 4 shows an enlarged cross sectional view of the balloon catheter 1 in an inflated state according to a further embodiment of the present invention.
Figure 12:
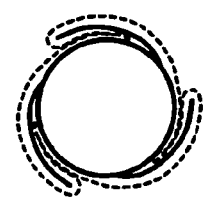
FIG. 8-FIG. 12 each illustrate a different subsequent folding position of the flap arrangement shown in FIG. 7.
Figure 11:
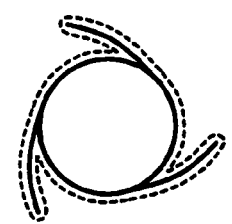
Figure 10:
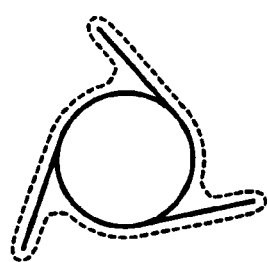
Figure 9:
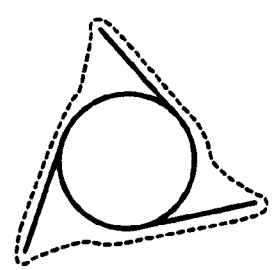
Figure 8:
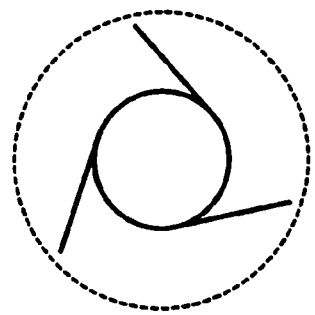

FIG. 4 shows an enlarged cross sectional view of the balloon catheter 1 in an inflated state according to a further embodiment of the present invention. In this embodiment, the flap arrangement 5 of the refolding device 4 arranged between the Ro-markers 11, 12, unlike the embodiment described in FIG. 3, takes a linearly offset wave form with longitudinally increasing/decreasing lengths of flaps 9, 10. The linearly offset wave form of the flap arrangement 5 provides the same advantages as the linear symmetrical waving shown in FIG. 3 above. Due to the offset wave form of the flap arrangement 5, the profile of the balloon catheter 1 is lowered in its deflated state, because during deflation the flaps of the refolding device 4 fit into linearly offset positions on the catheter tube 2. Moreover, the overall flexibility of the flap arrangement 4 is further improved by this structure.

Although not shown in the drawings, the flap arrangement 5 within the balloon 3 can alternatively be fixed on a flap tube (not shown) which is pushed over and fixed on the catheter tube 2.

FIG. 5 illustrates an isometric view of the inflated balloon folding mechanism on the catheter tube 2 including three tangentially protruding flaps 6, 7, 8 being separated into a plurality of flap portions 9, 10.

FIG. 6 illustrates an enlarged cross sectional view of the balloon catheter 1 in an inflated state according to a further embodiment of the invention. In this embodiment, the flap arrangement 5 of the refolding device 4 is aligned throughout the cylindrical section S of shown balloon 3. The flaps 6, 7 are either an integral part of the inner lumen 2 or can be fastened to the inner lumen 2. The balloon 3 can be deflated onto/against the folding mechanism, due to the flap length along the entire section S of the balloon 3.

FIG. 7 shows a further flap arrangement according to an embodiment of the present invention. The flaps 6, 7, 8 are equally spaced from each other and tangentially extending on the catheter tube (inner lumen) 2 to minimize the circumference and profile and protrude at an predetermined angle or tangentially to maximize the height of the flaps 6, 7, 8 when the balloon 3 wrapped around is inflated. This allows the balloon 3 to be folded accurately against the catheter tube 2 and to minimize the cross-sectional area thereof. The flaps 6, 7, 8 can have a thin uniform cross section along their entire length or have an increasing thickness or cross-section towards the inner tube to further increase their flexibility at their outer ends and to improve and assist a supported and guided refolding in all directions during deflation of the balloon 3.

FIG. 8-FIG. 12 respectively show different subsequent folding positions of the folding mechanism of the flap arrangement (6, 7, 8) depicted in FIG. 7 to illustrate the attitude thereof in the laboratory and during refolding in a patient's vessel.

The flaps of the above described embodiments should preferably be formed from a flexible and soft material such as nitinol, a polymer or a composite of a polymer and nitinol that is soft enough to force the balloon into proper refolding but flexible enough to fold and "stand up" upon balloon inflation without destroying the balloon material. As for the pleating and folding of the balloon, it has preferably to be done in a manner corresponding to the flap design used therein and wrapped in accordance with the flap arrangement.

In addition to the written disclosure, reference is herewith made explicitly to the disclosure of the invention in FIGS. 1 to 12.

The invention claimed is:

1. A balloon catheter comprising:
   a catheter tube;
   an inflatable and deflatable balloon fixed to said catheter tube; and
   a refolding device for folding the balloon onto said catheter tube during balloon deflation, wherein said refolding device includes at least one flap arrangement being fixed on said catheter tube and being disposed within said balloon, the at least one flap arrangement extends between Ro-markers disposed on the catheter tube and includes at least three flexible flaps fixed on said catheter tube, the at least three flexible flaps are circumferentially fixed and equally spaced from each other on the catheter tube, extend along a region of the catheter tube disposed in the balloon, are formed with predetermined lengths, each being formed in a bent or angled shape, and have decreasing cross sections along projecting lengths thereof.

2. The balloon catheter according to claim 1, wherein the flap arrangement takes a linear symmetrical wave form with longitudinally increasing/decreasing lengths of flaps.

3. The balloon catheter according to claim 1, wherein the flap arrangement takes a linearly offset wave form with longitudinally increasing/decreasing lengths of flaps.

4. The balloon catheter according to claim 3, wherein the flap arrangement is fixed on a flap tube fixed on said catheter tube.

5. The balloon catheter according to claim 4, wherein the three flexible flaps are each separated into flap portions.

6. A balloon catheter comprising:
   a catheter tube;
   an inflatable and deflatable balloon fixed to said catheter tube; and
   a refolding device for folding the balloon onto said catheter tube during balloon deflation, wherein said refolding device includes three flap arrangement being fixed on said catheter tube and being disposed within said balloon, the three flaps having a decreasing cross section a projecting length thereof.

7. The balloon catheter according to claim 6, wherein the three flap arrangement extends between radiopaque-markers disposed on the catheter tube.

8. The balloon catheter according to claim 6, wherein the three flaps are circumferentially fixed and equally spaced from each other on the catheter tube and extend along a region of the catheter tube disposed in the balloon.

9. The balloon catheter according to claim 6, wherein the three flaps have a predetermined length and are formed in a bent or angled shape.

10. The balloon catheter according to claim 6, wherein the three flexible flaps are arranged in a linear symmetrical wave form with longitudinally increasing/decreasing lengths of flaps.

11. The balloon catheter according to claim 6, wherein the three flexible flaps are arranged a linearly offset wave form with longitudinally increasing/decreasing lengths of flaps.

12. The balloon catheter according to claim 11, wherein the three flap arrangement is fixed on a flap tube fixed on said catheter tube.

13. The balloon catheter according to claim 12, wherein the three flexible flaps are each separated into flap portions.

14. A balloon catheter comprising:
   a catheter tube;

an inflatable and deflatable balloon fixed to said catheter tube; and a refolding device for folding the balloon onto said catheter tube during balloon deflation, wherein said refolding device includes at least one flap arrangement having a first end and a second end, the at least one flap arrangement being fixed on said catheter tube at the first end and the second end of the at least one flap arrangement and being disposed within said balloon.

15. The balloon catheter according to claim 14, wherein the flap arrangement extends between radiopaque-markers disposed on the catheter tube.

16. The balloon catheter according to claim 14, wherein the flap arrangement includes a plurality of flexible flaps being fixed on said catheter tube.

17. The balloon catheter according to claim 14, wherein the flap arrangement includes a plurality of flexible flaps circumferentially fixed and equally spaced from each other on the catheter tube and extend along a region of the catheter tube disposed in the balloon.

18. The balloon catheter according to claim 14, wherein the at least one flap has a predetermined length and is formed in a bent or angled shape.

19. The balloon catheter according to claim 14, wherein the flap arrangement comprises a plurality of flexible flaps have decreasing cross sections along the projecting lengths thereof.

20. The balloon catheter according to claim 19, wherein the flap arrangement takes a linear symmetrical wave form with longitudinally increasing/decreasing lengths of flaps.

21. The balloon catheter according to claim 19, wherein the flap arrangement takes a linearly offset wave form with longitudinally increasing/decreasing lengths of flaps.

22. The balloon catheter according to claim 21, wherein the flap arrangement is fixed on a flap tube fixed on said catheter tube.

* * * * *